United States Patent [19]

Satake

[11] Patent Number: 4,806,764

[45] Date of Patent: * Feb. 21, 1989

[54] APPARATUS FOR EVALUATING THE QUALITY OF RICE GRAINS

[75] Inventor: Toshihiko Satake, Higashihiroshima, Japan

[73] Assignee: Satake Engineering Co., Ltd., Tokyo, Japan

[*] Notice: The portion of the term of this patent subsequent to Jun. 21, 2005 has been disclaimed.

[21] Appl. No.: 190,134

[22] Filed: Apr. 22, 1988

Related U.S. Application Data

[63] Continuation of Ser. No. 24,139, Mar. 15, 1987, Pat. No. 4,752,689.

[30] Foreign Application Priority Data

Mar. 20, 1986 [JP] Japan ................................. 61-62785
Mar. 20, 1986 [JP] Japan ................................. 61-62786

[51] Int. Cl.⁴ ..................... G01N 21/35; G01N 21/47
[52] U.S. Cl. .................................. 250/339; 250/341; 250/358.1
[58] Field of Search ............... 250/339, 341, 358.1, 250/359.1; 356/445, 446, 448

[56] References Cited

U.S. PATENT DOCUMENTS 4,540,286  9/1985  Satake ............................. 356/445
4,692,620  9/1987  Rosenthal ........................ 250/339

Primary Examiner—Carolyn E. Fields
Attorney, Agent, or Firm—Wegner & Bretschneider

[57] ABSTRACT

This invention relates to an apparatus for evaluating the quality of rice grains. The apparatus comprises a near infrared spectrometer having a band-pass filter and detectors for detecting the intensity of reflected light from the sample rice; a control device having a memory for storing various values and a calculator for performing various calculations; indicating device for displaying or printing the various calculated values; and a sample case for being filled with the sample rice and being disposed at the measuring portion within the near infrared spectrometer. The apparatus is capable of measuring the content percentages of pre-selected constituent or constituents, such as, of protein, either amylose or amylopectin and moisture of the rice grains, calculating a quality evaluation value of the sample rice based on the measured and calculated values and powers established for the preselected constituents, and displaying the calculated evaluation value of the sample rice.

14 Claims, 7 Drawing Sheets

FIG.4

TABLE 2

| SAMPLE NO. | CONTENT PERCENTAGES (%) | | | PERSONAL JUDGE-MENT | APPARATUS EVALUA-TION |
|---|---|---|---|---|---|
| | AMYLOSE | PROTEIN | MOISTURE | | |
| 1 | 18.2 | 6.4 | 14.5 | 0.67 | 0.812 |
| 2 | 19.0 | 6.3 | 14.7 | 0.47 | 0.767 |
| 3 | 19.2 | 6.4 | 14.3 | 0.33 | 0.716 |
| 4 | 19.8 | 6.3 | 14.5 | 0.21 | 0.693 |
| 5 | 20.5 | 6.4 | 14.9 | -0.05 | 0.666 |
| 6 | 19.3 | 6.8 | 13.8 | 0.12 | 0.652 |
| 7 | 17.9 | 9.1 | 13.9 | 0.25 | 0.640 |
| 8 | 19.6 | 8.4 | 14.5 | -0.29 | 0.595 |
| 9 | 20.8 | 7.2 | 14.6 | -0.14 | 0.585 |
| 10 | 20.5 | 8.0 | 15.2 | -0.52 | 0.577 |
| 11 | 20.9 | 7.6 | 14.7 | -0.25 | 0.566 |
| 12 | 20.8 | 7.5 | 14.1 | -0.25 | 0.544 |
| 13 | 19.9 | 8.8 | 14.0 | -0.17 | 0.535 |
| 14 | 19.9 | 8.3 | 13.3 | -0.26 | 0.520 |
| 15 | 20.2 | 8.0 | 13.2 | -0.44 | 0.511 |
| 16 | 22.0 | 8.0 | 14.7 | -0.73 | 0.496 |
| 17 | 21.3 | 9.0 | 15.3 | -0.81 | 0.493 |
| 18 | 22.4 | 7.9 | 14.7 | -0.43 | 0.482 |
| 19 | 21.7 | 8.3 | 14.3 | -0.75 | 0.478 |
| 20 | 21.8 | 7.6 | 13.6 | -0.50 | 0.469 |
| 21 | 21.9 | 7.8 | 13.7 | -0.47 | 0.462 |
| 22 | 23.2 | 7.6 | 14.6 | -0.57 | 0.455 |
| 23 | 22.1 | 8.6 | 14.2 | -0.83 | 0.448 |
| 24 | 22.5 | 8.0 | 13.9 | -0.58 | 0.439 |
| 25 | 23.0 | 8.7 | 14.2 | -0.53 | 0.411 |

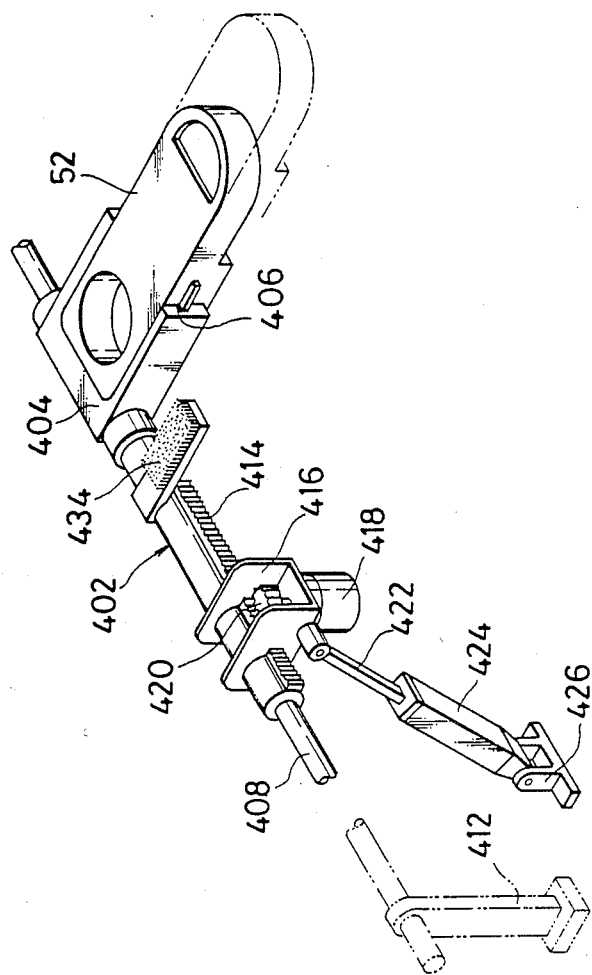

APPARATUS FOR EVALUATING THE QUALITY OF RICE GRAINS

This application is a continuation of Ser. No. 024,139, filed Mar. 10, 1987, now U.S. Pat. No. 4,752,689.

BACKGROUND OF THE INVENTION

The present invention relates to an apparatus for evaluating the quality of rice grains and is more particularly concerned with an apparatus for evaluating the quality of rice grains based on the measurements of the content percentages of pre-selected constituent(s) of rice grains.

The quality of rice grains, particularly in view of the taste when cooked, varies due to many different factors such as those relating to rice production, that is, selection of rice plant varieties, production districts, cultivation methods, harvesting methods, etc., those relating to rice grain processing after harvesting, that is, drying, storing, milling, etc., and those relating to the cooking of rice. As to the quality of rice grains, particularly from the view point of taste, those of the above relating to rice production have the most significant effect followed by those relating to rice grain processing.

Conventionally, the quality evaluation of rice grains, especially from the sense of taste of cooked rice, relied upon a personal examination and judgement according to an individual senses. The personal judgement means one in which a number of panel examiners repeatedly examine and evaluate the appearance, smell, taste, chewability, hardness, etc. of the sample grains to determine whether those being examined are superior or inferior as compared with reference grains for evaluation and the evaluation values thus obtained are averaged. However, as this personal judgement is effected based on a sense of taste which differs from person to person, the evaluation results obtained through the personal judgement can in no way be considered an objective and absolute value invariable regardless of time and place. Research has been developed which is intended to measure and analyze the constituents and the physicochemical properties of the rice grain for pursuing the correlation between the values thus measured and analyzed and the invention result obtained through personal judgement so that the quality of the rice grains may be evaluated on a scientific basis. As a consequence, it was found that the content ratio between amylose and amylopectin which constitute the starch content, content percentages of protein and content percentages of moisture are particularly important factors for purposes of evaluating the quality of rice grains.

Accordingly, how the difference of content percentages of various constituents of rice grains affect the quality, especially in terms of taste of rice grains after having been cooked, is discussed in detail hereunder.

Generally, the varieties of rice which are most popular in Japan from the view point of taste are "Koshihikari" and "Sasanishiki". As an example, the content percentages of protein and the content of amylose in 100% of the starch content of averagely milled white rice of several kinds of rice varieties including the above "Koshihikari" and Sasanishiki" are given in the following Table 1. It is, of course, needless to say that the same variety of rice does not necessarily contain the same content percentages of constituents as such content percentages become varied depending on the geological conditions (the soil and the water conditions) of the rice production districts and also on the atmospheric conditions (temperature, hours of sunshine, rainfall, etc).

TABLE 1

| VARIETIES | PRODUCTION DISTRICTS | CONSTITUENTS (%) | |
|---|---|---|---|
| | | Protein | Amylose |
| KoshiIhikari | Niigata | 6.70 | 19.9 |
| Sasanishiki | Yamagata | 6.89 | 20.9 |
| Nihonbare | shiga | 7.19 | 21.4 |
| Ishikari | Hokkaido | 8.48 | 23.2 |

In the Table, the content percentages of protein are shown by weight ratio while the content percentages of amylose are shown by ratio in 100% of the starch content.

From the above Table 1, it can be understood that the main factor accountable for the superiority of the taste of "Koshihikari" and "Sasanishiki" as compared with that of others resides in the fact that both the content percentages of the protein and the content ratio of the amylose in the starch are lesser as compared with those of other rice.

Besides the fact that the content percentages of protein and the content ratio of amylose in the starch significantly affect the taste of rice, that is, the quality of rice grains, the moisture content in the white rice also significantly affects the quality of rice, especially in relation to the chewability and hardness of cooked rice. When the moisture content of white rice is in the order of 15%, the rice grains do not develop cracks upon being immersed in water in a cooking pot so that the cooked rice remains in the best state. However, if the moisture content of the white rice is less than 14%, the rice grains are cracked instantaneously when they are immersed in water because of their rapid absorption of water. As soon as cracks develop in and through the rice grains, water is absorbed into such cracks. Broken rice grains also absorb water in the same way. When such rice grains are boiled, paste exudes out of the cracks and the boiled rice becomes watery, crumbly and too soft without any chewability. This problem of the content percentage of moisture of white rice grains becoming less than 14% may be mainly due to excess drying at the grain processing stage after harvesting, especially at the stage of drying operation, and also occurrence of cracking and heating due to friction during milling operation after the grain processing stage. Therefore, in order to avoid the quality of rice grains becoming lowered due to the content percentages of moisture being less than 14%, it is necessary that during drying process the drying machine be carefully controlled so that the grains do not become too dried and also that during milling process the milling machines be checked and regulated so that the rice grains are not broken due to the wearing out of the parts of the milling machines and there occurs no excess drying due to generation of heat. For the purposes of restoring the quality of rice grains whose content percentages of moisture have lowered to less than 14% due to such a reason as excess drying, there is commercially available a rice moistening machine. This machine is adapted to supply moisture to the white rice grains at a speed at which grains naturally absorb water or moisture so that the content percentages of moisture thereof is regulated up to around 15% which is the safe range for avoiding cracking in water.

In addition to the above explained content percentages of protein, starch and moisture of the rice grains which significantly affect the quality of rice grains, the content percentages of fat also affect the taste or quality of rice and it is usually said that lesser the content percentages of fat the better the taste. However, it can be said that the effect on the taste of the fat constituent is not so great as compared with that by the above three constituents.

Generally, since it is difficult to secure a single variety of rice grains of fine quality in a large amount for processing at a rice mill plant, rice grains of a number of varieties or a number of classes which are different in quality, for example, the rice grains believed to be of high grade and those believed to be of low grade, are blended with the blending ratio being appropriately controlled in an effort to produce a stable quality of white rice for distribution. However, the selection of rice varieties to be blended and the blending ratio therefor have been determined in the past based on personal judgement and data concerning the quality. In the absence of any methods that are supported from a scientific view point, the blended white rice thus produced for distribution has often tended to be irregular in quality and this has often been the subject of complaints by consumers.

On the other hand, as is conventionally well known and as is traditionally said, the taste of cooked rice is improved when ordinary rice (non-glutinous white rice) is added with a small amount of glutinous rice before cooking it and this is due to an increase in chewability. The following is a reason for this which is explained in relation to the changes in the content of chemical constituents of rice. The starch content consists of amylose and amylopectin and as is briefly explained hereinabove in connection with Table 1, the taste of rice tends to be inferior if the content ratio of amylose in 100% of the starch content becomes large. If a small amount of glutinous rice whose content ratio of amylopectin is approximately 100% is mixed into an ordinary rice whose content ratio of the same is 78%, the taste of the mixed rice is improved to almost the same as the rice which contains a larger amount of content ratio of amylopectin, that is, the rice which contains a smaller amount of content ratio of amylose. However, if the content ratio of amylopectin exceeds an appropriate amount, the cooked rice becomes too viscous and this causes a deterioration of the taste of rice.

From the above discussions, it may be understood that ideas have arisen that the evaluation of rice quality can be done by having the chemical constituents of rice grains measured and analyzed scientifically, that the rice grains of good taste can be discovered from among ordinary varieties of rice grains without the need to rely on specific famous varieties of rice grains which are generally known to be good tasting rice, and further that the quality, especially from the view point of the sense of taste, of rice grains can be improved by the blending of a plurality of varieties of rice grains or blending of a plurality of rice grains whose content percentages of constituents are different from one another.

OBJECTS OF THE INVENTION

A primary object of the present invention is to provide an apparatus for evaluating the quality of rice grains which is capable of measuring content percentages of a pre-selected constituent or constituents of rice grains in a short time, calculating an evaluation value based on the measured values and specific power or powers established correspondingly to the pre-selected constituent or constituents, and displaying the calculated evaluation value.

Another object of the present invention is to provide an apparatus for evaluating the quality of rice grains which is capable of measuring content percentages of preselected constituent or constituents, calculating and displaying an evaluation value based on the measured values and specific power or powers which are established correspondingly to the pre-selected constituent or constituents, and further calculating and displaying an appropriate blending ratio of a plurality of varieties of rice grains based on any desired conditions.

SUMMARY OF THE INVENTION

According to one aspect of the present invention there is provided an apparatus for evaluating the quality of rice grains based on the measured values obtained by measuring content percentages of a pre-selected constituent or constituents of rice grains comprising: a near infrared spectrometer having a light source, a band-pass filter allowing the passage of only such specific wavelengths of the light from the light source that are adapted to the measurement of content percentages of the constituents of the sample rice and producing near infrared monochromatic light to be incident on the sample rice at a measuring portion, and detecting means for detecting the intensity of reflected light from the sample rice at the measuring portion and producing detection signals; control means having a memory device for storing content conversion coefficients for the calculation of the content percentages established correspondingly to the pre-selected constituents and specific powers for the calculation of the quality evaluation values of the sample rice established correspondingly to the pre-selected constituents of the sample rice, and a calculation device for calculating the content percentages and the quality evaluation value of the sample rice grains based on the content conversion coefficients and the specific powers stored in the memory device as well as the detection signals from the detecting means; indicating means, connected to the control means, for visually displaying or printing the content percentages and the quality evaluation value of the sample rice grains calculated at the calculation device; and a sample case to be filled with the sample rice and disposed at the measuring portion of the near infrared spectrometer.

Therefore, anyone can obtain an accurate evaluation value for rice grains with ease and in a short time without relying on the above described personal judgement based on human sense of taste which definitely differs from person to person and also without performing any chemical quantitative analysis which requires considerable time and skill.

According to the present invention, the apparatus for evaluating the quality of rice grains may include an input means for inputting various information to be stored in the memory device of the control means. If the information is that for prime cost of various rice varieties as represented by sample rice grains and for desired conditions for blending such rice grains, the calculation device can calculate for displaying the blending ratio best suited to the desired conditions based on the information input through the input means.

Therefore, if the information input through the input means is that for kinds of rice to be blended and for a desired price of the recently blended rice, it is possible to obtain the best blending ratio for the best taste, that is, the best quality rice grains and, if the information input through the input means is that for the desired taste, that is, the desired quality of rice grains, after being blended, it is possible to obtain the information as to the kinds of rice and the blending ratio with which the most economical blending can be achieved. The operator can obtain scientifically such information which is accurate, without requiring him to be an expert and without a need to rely on personal judgement or data built from experience.

According to another aspect of the present invention there is also provided an apparatus for evaluating the quality of rice grains based on the measured values obtained by measuring content percentages of a preselected constituent or constituents of rice grains comprising: a near infrared spectrometer having a light source, a band-pass filter allowing the passage of only such specific wavelengths of the light from the light source that are adapted to the measurement of content percentages of the constituents of the sample rice and producing near infrared monochromatic light to be incident on the sample rice at a measuring portion, and detecting means for detecting the intensity of reflected light from the sample rice at the measuring portion and producing detection signals; control means having a memory device for storing content conversion coefficients for the calculation of the content percentages established correspondingly to the pre-selected constituents and specific powers for the calculation of the quality evaluation value of the sample rice established correspondingly to the preselected constituents of the sample rice, and calculation device for calculating the content percentages and the quality evaluation value of the sample rice based on the content conversion coefficients and the specific powers stored in the memory device as well as the detection signals from the detecting means; indicating means, connected to the control means, for visually displaying or printing the content percentages and the quality evaluation values of the sample rice grains calculated at the calculation device; a sample case to be filled with the sample rice and disposed at the measuring portion of the near infrared spectrometer; and a sample supplying means including a grinding means for grinding sample rice and filling the sample case with the ground sample and a sample rice positioning means for moving the sample case to and positioning the same at the measuring portion of the near infrared spectrometer.

When the above arrangements are employed for measuring the content percentages of the pre-selected constituents of rice grains, it is possible to automate the operation of grinding sample grains into powder and filling it in the sample case, which facilitates easier and more accurate measuring operation.

BRIEF DESCRIPTION OF THE DRAWINGS

The foregoing and other objects are effected by the invention as will be apparent from the following description and claims taken in connection with the accompanying drawings, forming a part of this application, in which:

FIG. 4 is a table, Table 2, showing the evaluation results concerning a plurality of varieties of rice grains contained through personal judgement as well as the evaluation values concerning the same obtained through the evaluation apparatus according to the present invention;

FIG. 9 is a perspective view of main parts of sample rice positioning means of the sample rice supplying means seen in FIG. 8.

DESCRIPTION OF THE PREFERRED EMBODIMENTS

Hereinafter, an apparatus for evaluating the quality of rice grains of a first preferred embodiment is explained by reference being made to the accompanying drawings, FIG. 1 to FIG. 5.

Figure 1:
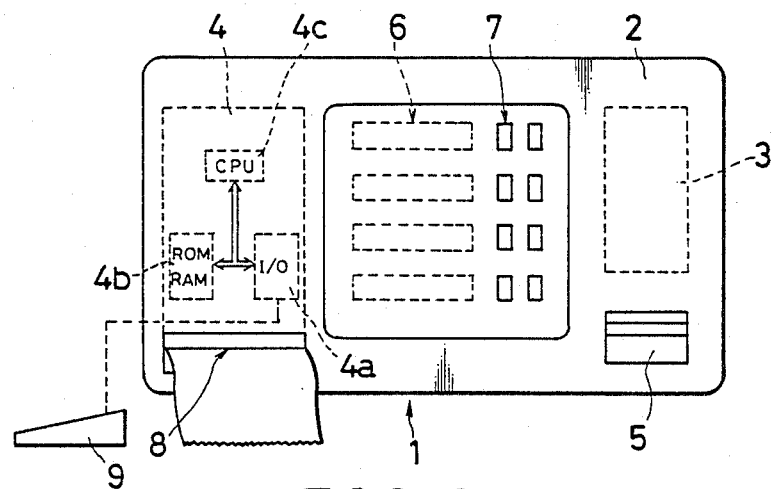
FIG. 1 is a front view schematically illustrating an apparatus for evaluating the quality of rice grains of the first embodiment according to the present invention.

FIG. 1 is a diagrammatic front view of an apparatus according to the present invention. Inside an cabinet 2, there is provided a near infrared spectrometer 3 which is explained in detail with reference to FIG. 2 and a control means 4. On a front panel of the cabinet 2, there are provided a sample holder 5 for carrying thereon a sample case in which a sample of rice to be measured is filled, an displaying means 6 of a LED or CRT type for visually displaying such information as operating procedures and various calculation results, a number of operating push buttons 7, and a printer 8 for printing out hard copies of the various calculation results. The control means 4 includes an input-output signal processing device 4a, a memory device 4b and a calculation device 4c. The input-output signal processing device 4a is connected to a light source, detectors of the near infrared spectrometer 3, the indicating means 6, the operating push buttons 7 and the printer 8 for processing various signals therebetween. The memory device 4b is for storing such information as content conversion coefficients for the calculation of the content percentages of pre-selected constituents of rice, specific powers for the calculation of the quality evaluation value of the sample rice established correspondingly to the pre-selected constituents of the sample rice, prime costs of different varieties or classes of rice to be input through an input means (keyboard) 9, and various compensation or calibration values and various operating procedures. The calculation device 4c is for making such calculation as the quality evaluation of sample rice based on the measured values obtained from the near infrared spectrometer 3 and the above-mentioned specific powers. The keyboard 9 as an input means is not necessarily required and this is so when, for example, the specific powers established individually for and correspondingly to the subject main constituents of rice and the necessary compensation or calibration values are memorized in advance in a read only memory (hereinafter referred to as "ROM") within the memory device 4b, the function required to the apparatus 1 is only the evaluation of the quality of sample rice grains and the function is not required as to the best blending ratio based on any desired conditions. Further, the printer 8 does not have to be a built-in type as it can be an externally connectable type.

Figure 2:
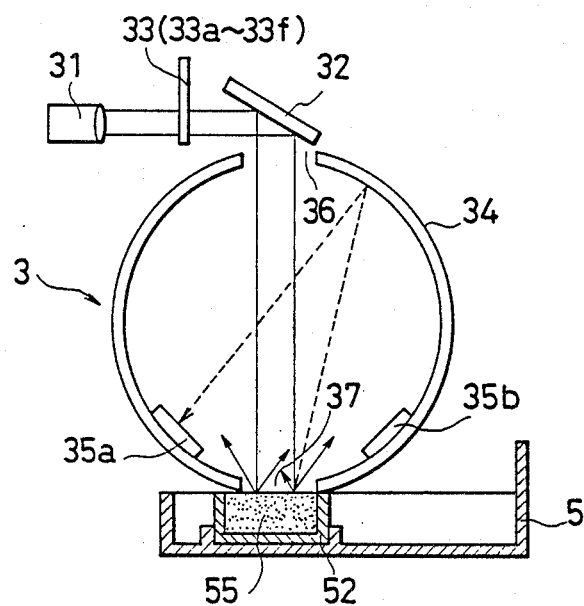
FIG. 2 is a sectional view of the near infrared spectrometer installed in the apparatus shown in FIG. 1.

FIG. 2 shows a partial sectional view of one example of the near infrared spectrometer 3 installed within the cabinet 2. The near infrared spectrometer 3 as illustrated is a reflection mode and posses as main components a light source 31, a mirror 32, a narrow range and-pass filter 33, an integrating sphere 34 and a pair of detectors 35a, 35b. The light emitted from the light source 31 becomes a parallel beam after passing through an appropriate optical system (not shown) and becomes a near infrared monochromatic light beam after passing through the band-pass filter 33. The near infrared monochromatic light beam changes its direction toward an inlet port 36 at a top of the intregrating sphere 34 by the mirror 32 which is capable of changing its inclination angle. The near infrared monochromatic light beams reflected at the mirror 32 and entered into the intregating sphere 34 through the inlet port 36 thereof are incident on a sample port, that is, a measuring portion 37 disposed at a bottom of the integrating sphere 34 and, thus, are incident from a position immediately above on the sample rice 55 in a sample case 52 positioned at a predetermined rear portion of the sample holder 5. Diffusely reflected light from the sample rice 55 reflects at an inner wall of the integrating sphere 34 and eventually reaches the detectors 35a, 35b provided in a pair symmetrically with respect to the center of the sample port-37 so that the intensity of the reflected radiation is measured thereby. In the illustrated example, there are provided a pair of detectors 35a and 35b for enabling the compensation of the optical symmetry and facilitating efficient receiving of the reflected radiation from the sample rice 55. However, the number of detectors is not limited to two and may be one or three or more.

Now, an explanation is made as to the construction and the physical properties required for the narrow range band-pass filter 33 which is positioned between the light source 31 and the mirror 32 and through which the light emitted from the light source 31 becomes near infrared monochromatic light beams having a specific wavelength. The band-pass filter 33 comprises any appropriate number of filters (for example, six filters 33a–33f) each of which has a different nominal wavelength as a passing property. These filters are mounted on a rotating flat disc so that, when it is rotated by an appropriate angle, any desired filter may be sequentially selected or replaced with the filter being positioned on the line crossing the light source 31 and the mirror 32. The nominal wavelength in passing properties of the filter means here the maximum passing wavelength out of near infrared light which passes when the angle of incidence is those of normal to the surface of the filter. Another example of the band-pass filter 33 is one which is rotatably arranged and in which polygonally formed mirrors 32 may be positioned within polygonally formed filters 33a–33f each of which is disposed facing to a surface of the corresponding one of the mirrors 32. When the band-pass filter 33 is in a rotating disc form, it can be arranged that the tilting angle of the disc surface with respect to the incident light axis be finely and continuously controllable by rotating means such as by a motor, and it is possible to produce near infrared monochromatic light beams of wavelengths continuously shifted from the nominal wavelengths which are of the respective filters. This is due to a well known phenomena in which, as the incident angle of colliminated light with respect to the filter surface deviates from 90°, the maximum wavelength passing through the filter shifts from the nominal wavelength within the ranges of tens of nanometers by the degrees corresponding to the deviated angles.

Figure 3:
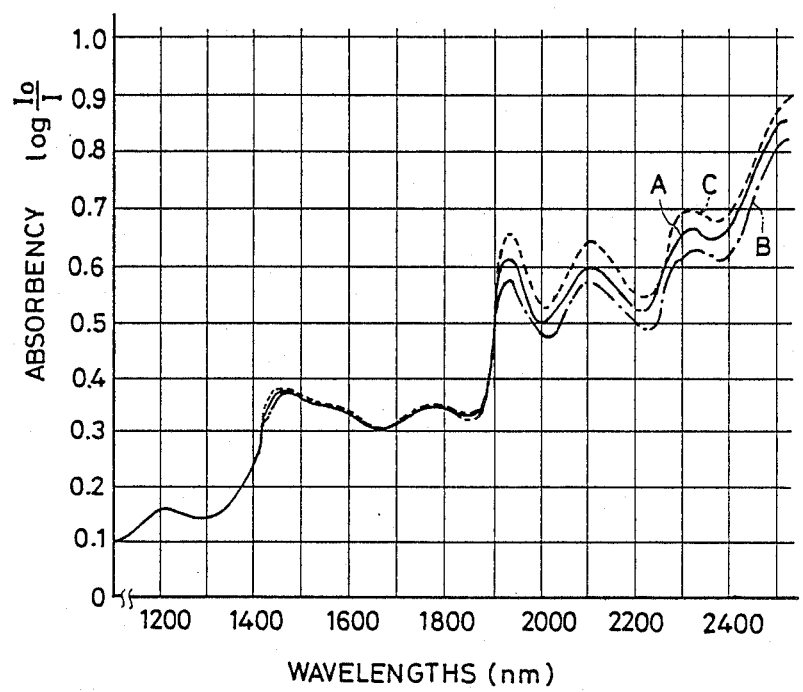
FIG. 3 is a graph of absorbency curves showing the relation between the wavelengths of near infrared light beam and the absorbency with respect to various varieties of rice grains.

Next, the physical properties required for the narrow range band-pass filter 33 will be explained hereinbelow by making reference to FIG. 3. FIG. 3 is a graph of absorbency curves showing the relation between the wavelengths of irradiation light beams and the absorbency when the near infrared light beam whose wavelength being continuously varied are irradiated on different samples of rice. The absorbency is the common cologarithm of the reference irradiation light amount (entire irradiation light amount $I_o$ to the reflected light amount I from the sample rice, that is, $\log I_o/I$. The cure A shown by a solid line corresponds to the rice variety "Nihonbare" whose content ratio of amylose in 100% of starch content is 21.4%, the curve B shown by one dot chain line corresponds to the variety "Koshihikari" whose amylose content ratio is 19.9% and the curve C shown by a dotted line corresponds to the variety "Ishikari" whose amylose content ratio is 23.2%, respectively. It can be clearly understood from FIG. 3 that as the short wavelength of near infrared light below 1900 nm is a region of low absorptivity, there are only slight differences in the absorptivity in amylose, protein, moisture, etc. which constitute rice grains but that, in a region of high absorptivity, with the 1900 nm as a dividing line, marked differences in the absorptivity are noted with the differences in the content percentages of such constituents. Accordingly, each of the filters 33a–33f of the band-pass filter 33 is required to have a nominal wavelength of each of the above described wavelengths as a specific wavelength passing characteristic so as to produce near infrared monochromatic light of the above described wavelengths each of which is adapted for the measurement of the respective constituents of rice grains.

Now, the actual operation of the apparatus for evaluating the quality of rice grains of the present invention having the above described constructions will be explained hereinafter. First of all, the light source 31 is turned on by the manipulation of the operating push button 7 so that the near infrared spectrometer 3 is entirely warmed up until the monochromatic light beams which are based on the light being emitted from the light source 31 and which reach the sample port 37 become stable. After the lapse of a predetermined time for the warming up of the apparatus, the sample case holder 5 is once drawn out from the cabinet 2 of the apparatus and then the sample case 52 which has already been filled with ground and powdered sample rice is positioned at the predetermined portion of the sample case holder 5, and lasty this sample case holder 5 carrying thereon the sample case 52 is inserted into the apparatus. The preparation work for the measurements is thus completed. It is desirable that the sample rice 55 be ground into fine particles of less than approximately 50 microns in diameter for avoiding the occurrence of errors in measurement values, however, it is not essential the sample rice 55 be always ground. It is desirable that, for the purposes of reducing the loss of light due to diffused reflection, the sample rice 55 which has been ground be filled in the sample case 52 so that the surface thereof becomes flat, and further that the surface of the sample rice 55 is covered by a transparent quartz plate with a slight pressure being added.

Upon the completion of the above explained preparation work for the measurements, firstly the filter 33a having 1940 nm as a nominal wavelength is selected so as to be positioned on the line crossing the light source 31 and the mirror 32 and the measurement of reflectance absorbency under the irradiation of monochromatic light beams of 1940 nm on the sample rice 55 is commenced. This measurement operation of reflection absorbency consists of two measurements, namely, one for the entire amount of light irradiated on the sample rice 55, that is, the reference irradiation light amount, and the other for the amount of light actually reflected by the sample rice 55 when the reference irradiation light beams are incident on the sample rice 55. It does not matter which of the two measurements take place first with respect to one filter, but in the following explanation the measurement for the reference irradiation light amount is made first. The measurement of the reference irradiation light amount is made in a state in which the inclination angle of the mirror 32 which is arranged to be variable is changed so that the reflected light therefrom may be directly incident on the inner wall of the integrating sphere 34 by way of an appropriate rotating means (not shown) such as a stepping-motor. By so doing the light from the mirror 32 incident directly on the inner wall of the integrating sphere 34 reaches eventually the detectors 35a, 35b after being diffusely reflected in all directions within the inner wall of the integrating sphere 34. The detectors 35a, 35b detect the diffusely reflected radiation as the reference irradiation light amount and produce electrical signals. On the other hand, the measurement of the amount of reflected light from the sample rice 55 is effected in accordance with the same principle as explained above after the inclination angle of the mirror 32 is returned to its original angle as shown in FIG. 2. It is needless to say that the sequential steps of the selection of the first filter to be used after the completion of the preparation work for measurements, the measurement of the reference irradiation light amount and the measurement of the amount of reflected light can be performed automatically in accordance with the programmed steps which are memorized in the ROM within the memory device 4b of the control means 4. If each of the measurements for the above mentioned reference irradiation light amount and the reflection light amount with respect to a given one filter is repeated and the average value is taken, this helps assuring the accuracy of the measured values. Each of the measured values based on the reference irradiation light amount and the reflection light amount from the the sample rice 55 detected by the detectors 34a, 35b is transferred to the control means 4 as the actually measured data for the calculation of each of the content percentages of protein, amylose and moisture which are main constituents of rice grains and is temporarily stored or accumulated in a random access memory (hereinafter referred to as "RAM") within the memory device 4b.

Upon the completion of the absorbency measurement under the irradiation wavelength of 1940 nm, the next procedure for absorbency measurement at another irradiation wavelength, that is, in this embodiment, at wavelength of 2030 nm is started. In this case also, the measurements of reference irradiation amount and the reflection light amount are effected in the same ways and with the same procedures as in the case of 1940 nm as explained above. The respective measured values are, as in the same way as in the above measurement, transferred to the control device 4 and they are temporarily stored in the RAM as the actual measurement data for the calculation of content percentages of the respective constituents. In the same manner as above, the absorbency measurements for the respective remaining wavelengths of 2100 nm, 2130 nm, 2270 nm and 2370 nm are successively performed in this order and the respective values thus obtained are transferred to the control means 4 and they are accumulated in the RAM thereof as the actual measurement data. The changing or selecting operation of each of the filters 33a–33f mounted on the band-pass filter 33, required in the course of the absorbency measurement from the one specific wavelength to the other specific wavelengths, is generally performed automatically in accordance with the operation programs memorized in advance in the ROM within the memory device 4b of the control means 4. However, in this embodiment also, it is not necessary that the absorbency measurements be performed for all of the abovementioned six wavelengths. The wavelength or wavelengths under which the absorbency measurements take place can be chosen selectively taking into account the accuracy required for the evaluation value or the measurement time needed. Such choice of the measurement wavelength may be made by the manipulation of a wavelength selection button of the operating push buttons 7.

Although the measurement of absorbency as explained hereinabove is a spot-type measurement in which each of the six filters 33a–33f of the band-pass filter 33 is alternatively or sequentially selected so as to conduct absorbency measurement under each of the nominal wavelengths thereof, it is also possible to conduct a continuous absorbency measurement in the wavelength region 1900–2500 nm in which the differences in contents clearly appear as absorbency differences due to the above described phenomena in which the maximum passing wavelength shifts from the nominal wavelength of the filter in the ranges of tens of nanometers when the angle of incidence with respect to the surface of the filter is changed from the reference angle, that is, the angle normal to the filter surface. In this first embodiment shown in the drawings, such a continuous absorbency measurement can be realized by the adoption of an arrangement in which the tilting angle of the disc-shaped band-pass filter 33 is finely and variably changed by an appropriate control device (not shown) such as a motor based on the control signals sent from the control means 4 so that the incident angle of light beam incident on the filter surface is varied.

Subsequently, the calculation device 4c of the control device 4 calculates the respective content percentages of amylose, protein and moisture which are important constituents for obtaining an evaluation value of rice quality, based on the number of the actual measurement data obtained through the absorbency measurements and stored in the RAM within the memory device 4b as well as the content conversion coefficients memorized in advance in the ROM of the same memory device 4b for the calculation of the respective content percentages. The above content conversion coefficients, which are correspondingly set to the respective constituents and memorized in advance in the ROM of the memory device 4b, are those which are obtained by the processing of the measurement values of the absorbency detected by the detectors and by the carrying out of the multiple regression analysis on the thus processed values using as references the content percentages of the respective constituents for a number of rice samples which content percentages have been measured by, for example, a chemical quantitative analysis. Next, the calculation device 4c calculates a quality related value K in accordance with the following Equation (1) based on the content percentages of amylose, protein and moisture which have been obtained as above.

$$K = \left(\begin{array}{c}\text{amylose} \\ \text{content percentages}\end{array}\right)^A \times \left(\begin{array}{c}\text{protein} \\ \text{content percentages}\end{array}\right)^B \times \left\{15 + \left|15 - \left(\begin{array}{c}\text{moisture} \\ \text{content percentages}\end{array}\right)\right|\right\}^C \quad (1)$$

In the above equation (1), the powers A, B and C are established for the calculation of the quality evaluation value and they are to be memorized in advance in the ROM within the memory device 4b or to be input into the control means 4 through the input means 9 when the measurement of the sample rice are to take place. The powers A, B and C are values which have been calculated in advance based on the known quality evaluation results and content percentages, and these powers A, B and C for white rice and those for unmilled or brown rice may be different. For example, in evaluating the quality of Japanese white rice, the above powers A, B, C applied to the Equation (1) are 1.0, 0.3, 0.75 respectively as suitable values. However, in some cases, different values for these powers may be more suitable because the standards of tastes for rice may naturally be different from country to country where such rice is eaten.

The calculation device 4c further calculates based on the quality related value K obtained through the above Equation (1), the quality evaluation value T in accordance with an Equation (2) given below. The quality evaluation value T means that the greater the value the better the taste or the quality of rice grains.

$$T = 50,000/K^2 \quad (2)$$

The quality evaluaton value T as well as the respective content percentages of amylose, amylopectin and moisture, the content percentages being obtained in the course of the calculation of the value T, which have been calculated in accordance with the abovementioned Equations (1) and (2) are visually displayed on the displaying means 6 upon the completion of the calculating operation in the calculation device 4c and, further, a hard copy thereof can be produced automatically or upon the operator's command on the operating push button 7. As to the content percentages of amylose, the content ratio of amylose against that of amylopectin in 100% of the starch content, which constitutes starch together with amylose, is a more significant value than the content percentages itself of amylose. Therefore, for amylose, it is desirable that the indication therefor provided on the displaying means 6 is by way of content ratio in 100% of the starch rather than content percentages.

Figure 5:
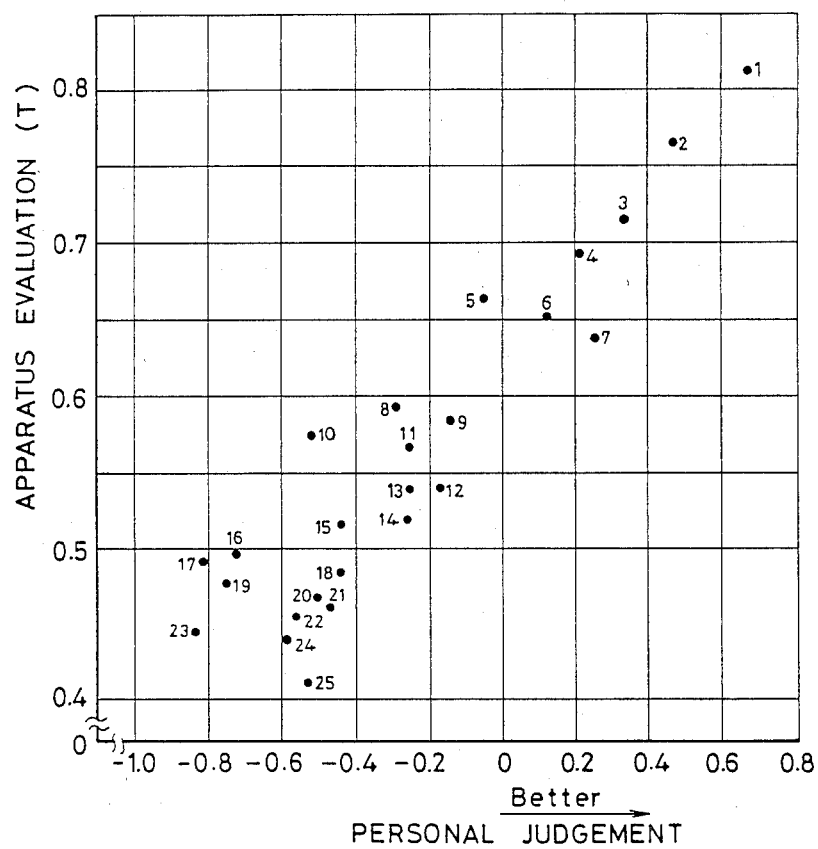
FIG. 5 is a plotted graph showing the relation between the evaluation results obtained through personal judgement and the evaluation values obtained through the evaluation apparatus, both evaluation results and values being given in Table 2.

Table 2 of FIG. 4 shows the evaluation results obtained through the conventional personal judgement conducted on twenty five varieties (different in brand or production districts, etc.) of rice grains. It also shows the content percentages of the respective constituents measured and calculated through the rice quality evaluation apparatus according to the present invention and the quality evaluation values calculated by the same based on the above content percentages for the same rice grains. The sample numbers of the rice grains in Table 2 were assigned in the order of the rice gains which have higher evaluation values calculated by the apparatus of the present invention, that is, those are determined as high quality rice grains. FIG. 5 is a plotted graph indicating both the evaluation results obtained through personal judgement and the evaluation values obtained through the apparatus of the present invention given in FIG. 4 so as to show the correlation therebetween. The number given to each of the points indicating the evaluation result or value on the graph corresponds to the relevant number in Table 2 of FIG. 4. It can clearly be understood, from the table 2 of FIG. 4 and more particularly from the graph of FIG. 5, that there is a proportional correlation between the evaluation results and the evaluation values.

After the sample rice grains of a number of kinds or varieties or those produced in different districts are measured, their respective qualities are evaluated and these data are stored in the RAM of the memory device 4b, any desired conditions such as kinds or varieties of rice grains to be blended or any desired prices may be input through the inputting means (key board) 9. Then, the calculation device 4c of the control means 4 carries out the calculation of the best blending ratio which satisfies the pre-established conditions, hence the best taste rice or best quality rice based on the prime costs of rice grains for blending as memorized in advance in the ROM and the data stored or accumulated in the RAM. This blending ratio is indicated on the displaying means 6. When the established conditions input through the input means 9 relate to the desired taste or the desired quality to be obtained by the blending of various kinds of rice grains, the control means 4 makes the calculation for kinds of rice grains which are lowest in price and the blending ratio thereof based on the prime costs of rice grains to be blended as memorized in advance in the ROM and the data stored in the RAM. This ratio is also indicated on the displaying means 6. Further, it is of course possible to print out the result of any calculation, either automatically or by the manipulation of the operating push button 7, by the printer 8 in addition to the visual indication on the displaying means 6. The data such as the content percentages and the quality evaluation values of a various sample rice grains calculated by the quality evaluation apparatus may be stored in an external memory means such as a floppy disk system. When the blending ratio of various rice grains is calculated, the data stored in the external memory means may be read into the RAM of the memory device 4b within the apparatus and the necessary calculation may be carried out based thereon.

Further, the above explanation has been made with respect to the sample rice in a ground or powdered form, but it is not limited that the rice grains be in that form. However, in such a case, the accuracy of the resulted evaluation values of rice quality may be lowered to some extent.

Next, the second embodiment of the apparatus for evaluating the quality of rice grains according to the present invention is explained hereinafter by making reference to FIG. 6 to FIG. 9. The same reference numerals are used for the like means or parts appearing in the explanation of the apparatus of the first embodiment.

The apparatus of the second embodiment differs from that of the first embodiment mainly in that the apparatus of the second embodiment additionally includes a sample grain grinding means for grinding and reducing into powder the sample grains and a sample rice positioning means for automatically moving to and positioning at the measuring portion of a infrared spectrometer 3 a sample case in which the ground and powdered sample rice is filled.

Figure 6:
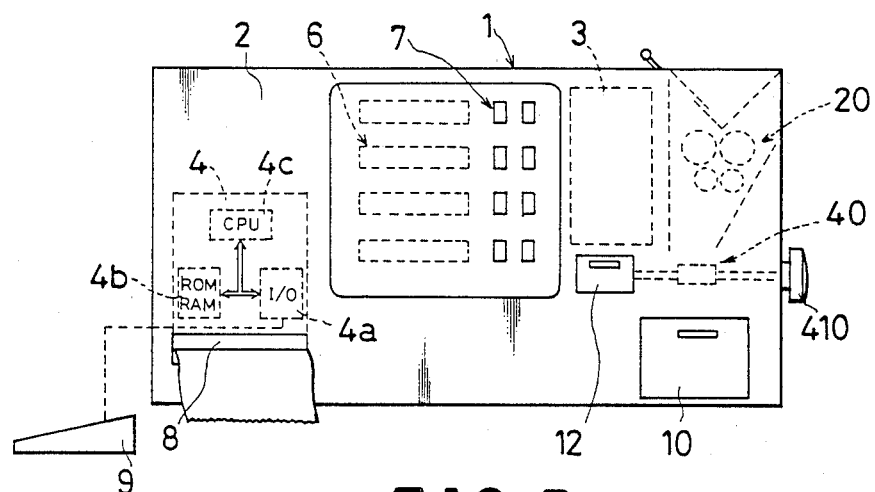
FIG. 6 is a front view schematically illustrating an apparatus for evaluating the quality of rice grains of the second embodiment according to the present invention.

As shown in FIG. 6, a box 10 is for receiving any excess of the powdered sample after the necessary amount thereof has been filled in the sample case and also for receiving the sample after it has been discharged upon completion of the measuring operation. This box 10 can be drawn in and out from the front panel of a cabinet 2. The numeral 12 represents an external supplying means through which a separately prepared sample of rice is supplied from outside the apparatus. The numerals 20 and 40 respectively represent a sample grain grinding means and a sample rice positioning means, both of which are disposed within the cabinet 2.

Figure 7:
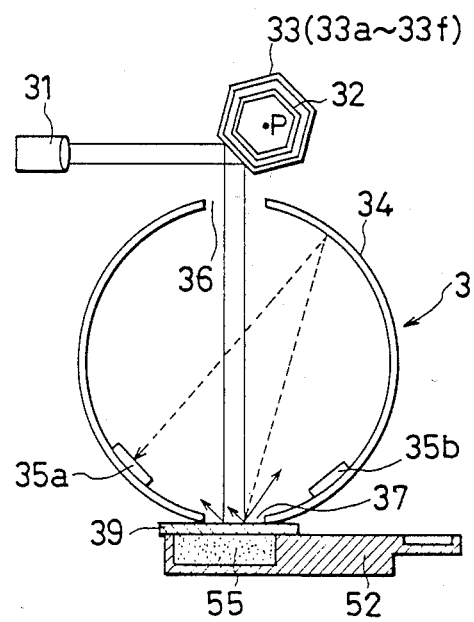
FIG. 7 is a sectional view of the infrared spectrometer installed in the apparatus shown in FIG. 6.

FIG. 7 is a cross-sectional view of a near infrared spectrometer 3 used in the apparatus of this second embodiment. The difference from the near infrared spectrometer 3 used in the first embodiment is that there is arranged a band-pass filter 33 which consists of a plurality of filters 33-33f and which is not in a rotating disc form but in a rotating polygonal form. The band-pass filter 33 posses inside thereof a plurality of mirrors 32 which are arranged in a polygonal form so that each of the mirrors 32 faces to the corresponding one of the filters 33a-33f. The band-pass filter 33 together with the mirrors 32 can rotate about the axis P of the polygonal filter by means of a rotating means (not shown) such as a stepping-motor connected thereto. A measuring portion 37 of an integrating sphere 34 is covered by a quartz transparent plate 39. In the near infrared spectrometer 3 of the first embodiment, since the grinding operation of a sample rice as well as the filling-in operation are done separately outside the apparatus, a cover plate such as the transparent plate 39 was not necessarily required for covering the measuring portion 37. However, in the apparatus of the second embodiment, since the grinding of sample rice and the filling of the sample in the sample case are done all within the apparatus, it is important that the transparent plate 39 over the measuring portion 37 in order to prevent scattered powder from entering into the integrating sphere 34 and adhering on the inner wall thereof.

Figure 8:
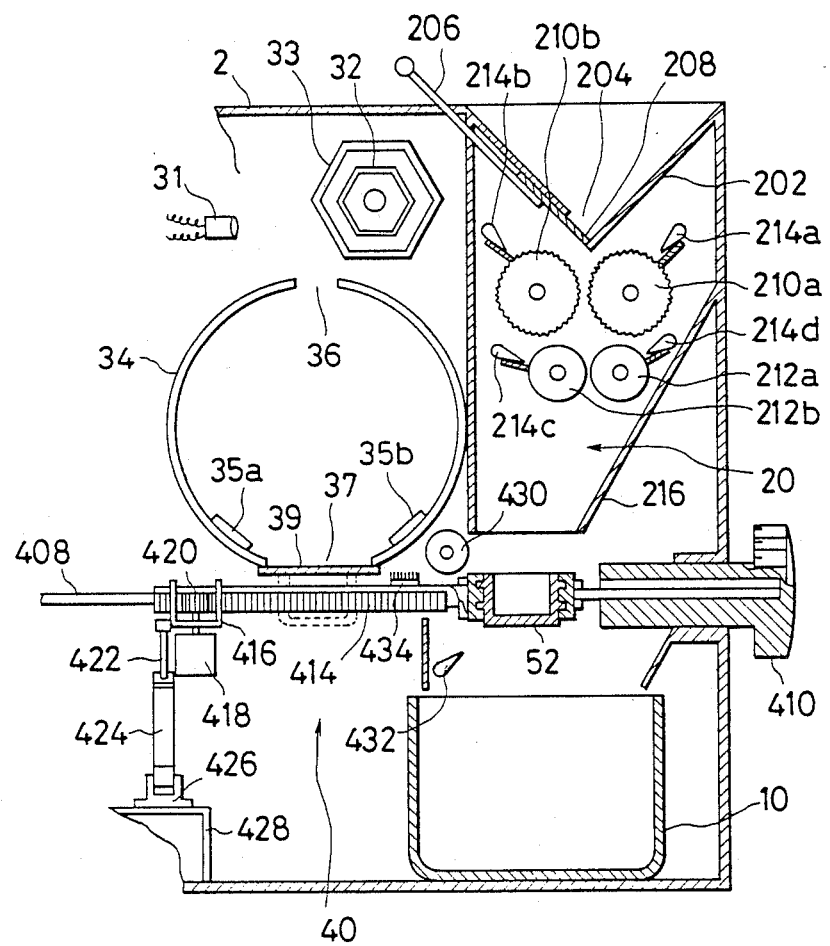
FIG. 8 is a sectional view of main parts of sample rice supplying means employed by the apparatus shown in FIG. 6.

Next, a sample rice supplying means is hereinafter explained with reference to FIG. 8 and FIG. 9. FIG. 8 is a sectional view of main portions of the near infrared spectrometer 3 and the sample rice supplying means and FIG. 9 is a perspective view of main portions of the sample rice positioning means 40.

Firstly, the construction of the sample grain grinding means 20 of the sample rice supplying means is explained. The cabinet 2 has at its right upper portion an opening at which a hopper 202 is mounted. At a bottom opening 204 of the hopper 202, there is provided a shutter 208 operable by a manual lever 206 or a magnetic solenoid (not shown). Below the opening 204 of the hopper 202, there are axially provided a pair of grinding rollers 210a, 210b, which are disposed face to face and which have a large number of sharp projections on their surfaces. At a position further downward, there are axially provided a pair of fine grinding rollers 212a, 212b which have smooth surfaces and which are provided face to face. The axes of each of the grinding rollers 210a, 210b and the fine grinding rollers 212a, 212b are driven by motors (not shown). The sample rice adhering on the surfaces of the grinding rollers 210a, 210b and also the fine grinding roller 212a, 212b is removed by cleaning devices 214a-214d which are constituted by jet nozzles provided facing to the surfaces of the respective rollers and elastic blade members provided so as to be lightly in contact with the surfaces of the respective rollers. All of these constituent parts are surrounded by a case member 216 a bottom portion of which is opened toward a sample rice positioning means 40 which is explained hereinbelow.

Here, an explanation is made of the sample rice positioning means 40 in which the sample rice finely ground at the sample grain grinding means 20 is filled in a sample case 52 so as to be in a state in which the measurement of absorbency is possible and such sample case 52 is moved to a position immediately below the measuring portion 37 of the near infrared spectrometer 3. The sample case 52 is slidably inserted in guiding grooves 406 of a case holder 404 fixed to a sampler case moving guide 402. A supporting bar 408 of a round shape in its crosssection is inserted in a hollow portion of the sample case moving guide 402 and one end of the supporting bar 408 is held by a rotating handle 410 whereas the other end of the supporting bar 408 is rotatably held by a bearing base 412. On a longitudinal peripheral surface of the sample case moving guide 402, there are racks 414 which are in engagement with pinion gears 420 of a motor 418 mounted on a motor holding member 416 movably held on the sample case moving guide 402. The motor holding member 416 is connected to a pivotal support base 426 through an electromagnetic member 424 having a telescopic rod 422. This pivotal support base 426 is fixed to the receiving base 428 at a bottom wall of the cabinet 2. The numeral 430 represents a roller which is for pressing filling the finely ground sample rice in the sample case 52 and for removing any excess sample rice as well as smoothing the upper surface of the sample rice. The numeral 432 is a jet nozzle which is for blowing away the sample rice into the sample case 52 upon completion of the measuring operation so as to clean the sample case 52. The numeral 434 is a cleaner which cleans a transparent plate 39 by contacting the same when the sample case 52 travels.

Next, an explanation will be made to the actual operation of the apparatus of the second embodiment of the present invention. As to the method of measurements of an absorbency at each of the wavelengths with the use of the near infrared spectrometer 3 is the same for the apparatus of the first embodiment, the same explanation is not repeated. Here, an explanation is centered around the function and operation of the sample rice supplying means which is one of the features of the second embodiment of the present invention.

Sample rice grains are introduced into the hopper 202. Then, the motor is switched on to rotate the grinding rollers 210a, 210b and the fine grinding rollers 212a, 212b. By manipulating the operating push button 7, the motor 418 is rotated thereby to move the sample case 52 to a position immediately below the sample grain grinding means 20. When the sample case 52 has moved to the predetermined position and the motor 418 has stopped, the shutter 208 is opened by way of the manual lever 206 or the magnetic solenoid (not shown) and the sample rice grains flow down from the hopper 202 through the opening 204. The sample rice grains thus flowed down from the hopper 202 are ground firstly by the grinding roller 210a, 210b and then by the fine grinding rollers 212a, 212b located under the first mentioned rollers 210a, 210b. The sample rice grains are thus ground into fine particles of less than approximately 50 microns in diameter as required for absorbency measurements. The sample in powder thus prepared is received in the sample case 52 located therebelow. The excess sample overflowed from the sample case 52 is received by the receiving box 10. Next, by the operation of the push button 7, the motor 418 is started again so that the sample case 52 filled with the sample rice is moved to a position immediately below the measuring portion 37 of the near infrared spectrometer 3. In the course of the movement of the sample case 52, the sample built up above the brim thereof is removed and the surface of the sample is flattened or smoothed by the roller 430 with the light pressure given thereto. When the sample case 52 is brought in position, the motor 418 automatically stops.

The sample rice 55 brought to the measuring portion 37 of the near infrared spectrometer 3 by the sample rice positioning means 40 is subjected to the absorbency measurement and the calculation of the content percentages of the subject constituents and the quality evaluation is carried out based on the same principle as explained above in connection with the apparatus of the first embodiment. The calculation of the quality evaluation is, of course, made based on the same Equations (1) and (2) as explained for the first embodiment.

When the absorbency measurement of the sample rice 55 is completed, the motor 418 is started again so that the sample case 52 is moved to a position immediately below the sample grain grinding means 20 for effecting the disposal of the used sample. In the course of this operation, the cleaner 434 touches and slides on the transparent plate 39 and anything adhering on the surface of the plate 39 is removed. As soon as the motor 418 stops with the sample case 52 having reached a position immediately below the sample grain grinding means 20, the cleaning devices 214a-214d within the sample grain grinding means 20 eject the high pressure jet air and, thus, each of the rollers 210a, 210b, 212a, 212b is cleaned. Next, by the energization of the electromagnet member 424, the sample case moving inside guide 402 is rotated 90 degrees so that the sample rice in the sample case 52 is discharged out into the receiving box 10. At the same time, by the jet nozzle 423, the inner wall of the sample case 52 is cleaned for the next measurement operation. So far, it has been explained as to how the sample case 52 is moved back and forth automatically by the operation of the motor 418. However, this movement can well be effected manually by a pushing action of the handle 40 and also the discharging of the sample from the sample case 52 can be effected by manually rotating the same. When the built-in sample rice supplying means is not used and a sample prepared separately outside the apparatus is to be placed at the measuring portion 37 of the near infrared spectrometer 3, the sample case 52 is first moved to a position immediately below the measuring portion 37 by the pushing action of the handle 410, the sample case 52 is drawn out from the external supplying means 12, and the same is filled with the sample and inserted into the guide grooves 406 of the sample case holder 404.

In the apparatus of the first and second embodiments explained above, although the near infrared spectrometer employed is of a reflectance mode which measures the intensity of the reflected light from the sample for measuring the absorbency of the light when infrared monochromatic light beam having a specific wavelength is irradiated on the sample rice, it is possible to employ a near infrared spectrometer of a transmittance mode with which the intensity of light transmitted through the sample is measured. Further, it is possible to employ a more accurate near infrared spectrometer in which an arrangement of the reflectance and transmittance modes is adopted for measuring the absorbency.

In the above, it has been explained how the rice quality is evaluated based on the analysis of amylose which, together with amylopectin, constitutes the starch content of rice. However, instead of the amylose, it is possible to measure the content percentages of amylopectin and establish the specific power to be applied in the Equation (1) for achieving the same purpose as above.

Further, in addition to the starch contents (amylose or amylopectin), protein and moisture, if any other constituents such as fat is to be measured for its content percentages, a specific power may be established therefor. In this way, better accuracy for the quality evaluation can be ensured. Conversely, it may also be possible to measure the content percentages of any one or two out of starch content, protein and moisture for purposes of the same evaluation but usually the accuracy obtained may not be as good as in the case as explained above.

While the invention has been described in its preferred embodiment, it is to be understood that the words which have been used are words of description rather than limitation and that the changes within the purview of the appended claims may be without departing from the true scope and spirits of the invention in its broader aspects.

What is claimed is:

1. An apparatus for evaluating the quality of rice grains based on the measured values obtained by measuring content percentages of a pre-selected constituent or constituents of rice grains comprising:

a near infrared spectrometer having a light source, a band-pass filter allowing the passage of only such specific wavelengths of the light from said light source that are useful for the measurement of content percentages of the constituents of the sample rice grains and producing near infrared monochromatic light to be incident on the sample rice at a measuring portion, and detecting means for detecting the intensity of reflected light from said sample rice at said measuring portion and producing detection signals;

control means having a memory device for storing content conversion coefficients for the calculation of the content percentages established correspondingly to said pre-selected constituents and specific powers for the calculation of the quality evaluation values of the sample rice established correspondingly to said pre-selected constitutents of said sample rice, and calculation device for calculating the content percentages and the quality evaluation values of the sample rice grains based on said content conversion coefficients and said specific powers stored in said memory device as well as said detection signals from said detecting means;

indicating means, connected to said control means, for visually displaying or printing said quality evaluation values of said sample rice grains calculated in said calculation device; and a sample case to be filled with said sample rice and disposed at said measuring portion of said near infrared spectrometer.

2. An apparatus for evaluating the quality of rice grains according to claim 1, in which said band-pass filter has specific wavelength passing properties for measuring, out of constituents of the sample rice, at least content percentages of protein, content percentages of either amylose or amylopectin, and content percentages of moisture.

3. An apparatus for evaluating the quality of rice grains according to claim 2, in which said band-pass filter has a tilting angle which provides an angle of incidence which is variable with respect to a surface of said filter.

4. An apparatus for evaluating the quality of rice grains according to claim 1, in which said band-pass filter disposed between said light source and said measuring portion of said near infrared spectrometer is such that its tilting angle is variable for varying an angle of incidence with respect to a surface of said filter.

5. An apparatus for evaluating the quality of rice grains according to claim 1, in which said band-pass filter is constituted by a plurality of filters each of which has a given wavelength as a nominal wavelength in the wavelength region 1900–2500 nm, each of said plurality of filters being in a rotating disc form.

6. An apparatus for evaluating the quality of rice grains according to claim 1, which further comprises an inputting means for inputting information in the memory device of said control means.

7. An apparatus for evaluating the quality of rice grains according to claim 6, in which said inputting means inputs into said memory device information on costs of rice grains represented by the sample rice grains and conditions for blending them and said calculation device calculates the most suitable blending ratio based on the input information.

8. An apparatus for evaluating the quality of rice grains based on the measured values obtained by measuring content percentages of a pre-selected constituent or constituents of rice grains comprising:

a near infrared spectrometer having a light source, a band-pass filter allowing the passage of only such specific wavelengths of the light from said light source that are useful for the measurement of content percentages of the constituents of the sample rice grains and producing near infrared monochromatic light to be incident on the sample rice at a measuring portion, and detecting means for detecting the intensity of reflected light from said sample rice at said measuring portion and producing detection signals;

control means having a memory device for storing content conversion coefficients for the calculation of the content percentages established correspondingly to said pre-selected constituents and specific powers for the calculation of the quality evaluation values of the sample rice established correspondingly to said pre-selected constituents of said sample rice, and calculation device for calculating the content percentages and the quality evaluation values of the sample rice grains based on said content conversion coefficients and said specific powers stored in said memory device as well as said detection signals from said detecting means;

indicating means, connected to said control means, for visually displaying or printing said quality evaluation values of said sample rice grains calculated in said calculation device;

a sample case to be filled with said sample rice and disposed at said measuring portion of said near infrared spectrometer; and a sample rice supplying means including a sample grain grinding means for grinding sample rice grains and filling said sample case with the ground sample and a sample rice positioning means for moving said sample case to and positioning the same at the measuring portion of said near infrared spectrometer.

9. An apparatus for evaluating the quality of rice grains according to claim 8, in which said sample grain grinding means includes at an upper portion thereof a hopper for feeding sample rice grains, a pair of grinding rollers disposed face to face below said hopper, and a pair of second rollers disposed face to face below said grinding rollers for reducing the ground grains into powder.

10. An apparatus for evaluating the quality of rice grains according to claim 8, in which said band-pass filter has specific wavelengths passing properties for measuring, out of constituents of the sample rice, at least content percentages of protein, content percentages of either amylose or amylopectin, and conent percentages of moisture.

11. An apparatus for evaluating the quality of rice gains according to claim 8, in which said band-pass filter disposed between said light source and the measuring portion of said near infrared spectrometer is such that its tilting angle is variable for varying an angle of incidence with respect to a surface of said filter.

12. An apparatus for evaluating the quality of rice grains according to claim 8, in which said band-pass filter is constituted by a plurality of filters each of which has a given wavelength as a nominal wavelength in the wavelength region 1900–2500 nm, and each of said plurality of filters being in a rotating polygonal form.

13. An apparatus for evaluating the quality of rice grains according to claim 8, which further comprises an inputting means for inputting information in the memory device of said control means.

14. An apparatus for evaluating the quality of rice grains according to claim 13, in which said inputting means inputs into said memory device information on costs of rice grains represented by the sample rice grains and conditions for blending them and said calculation device calculates the most suitable blending ratio based on the input information.

* * * * *